United States Patent [19]

Stratton

[11] Patent Number: 4,891,177
[45] Date of Patent: Jan. 2, 1990

[54] WATER-FLOOD SURFACTANT

[75] Inventor: Charles A. Stratton, Dewey, Okla.

[73] Assignee: Mary Rose Stratton, Dewey, Okla.

[21] Appl. No.: 54,188

[22] Filed: May 26, 1987

[51] Int. Cl.[4] .................... C07C 143/24; C07C 43/11; C07C 43/18; C07C 43/20

[52] U.S. Cl. .................... 252/8.515; 568/608; 252/8.552; 252/8.554; 252/311.5; 252/351; 252/170; 210/749

[58] Field of Search .................... 568/608; 260/505 R

[56] References Cited

FOREIGN PATENT DOCUMENTS 694525 9/1964 Canada .................... 568/608

Primary Examiner—Ronald W. Griffin
Attorney, Agent, or Firm—William S. Dorman

[57] ABSTRACT

A water-flood surfactant and the method of making it which comprises the steps of mixing, in a reactor, sodium hydroxide with a sulfonated natural petroleum crude, the sodium hydroxide being in excess of the amount required to convert the sulfonate to phenol and sufficient to convert a portion of the phenol to sodium phenolate; heating the mixture while stirring to about 319° C. for a period of about one hour; passing a current of inert gas through the top of the reactor during the heating step; cooling the mixture to a temperature of approximately 200° C. while continuing to pass an inert gas through the top of the reactor; and passing ethylene oxide gas through the mixture in the reactor while maintaining the temperature in the reactor between 200° C. and 220° C.

19 Claims, 1 Drawing Sheet

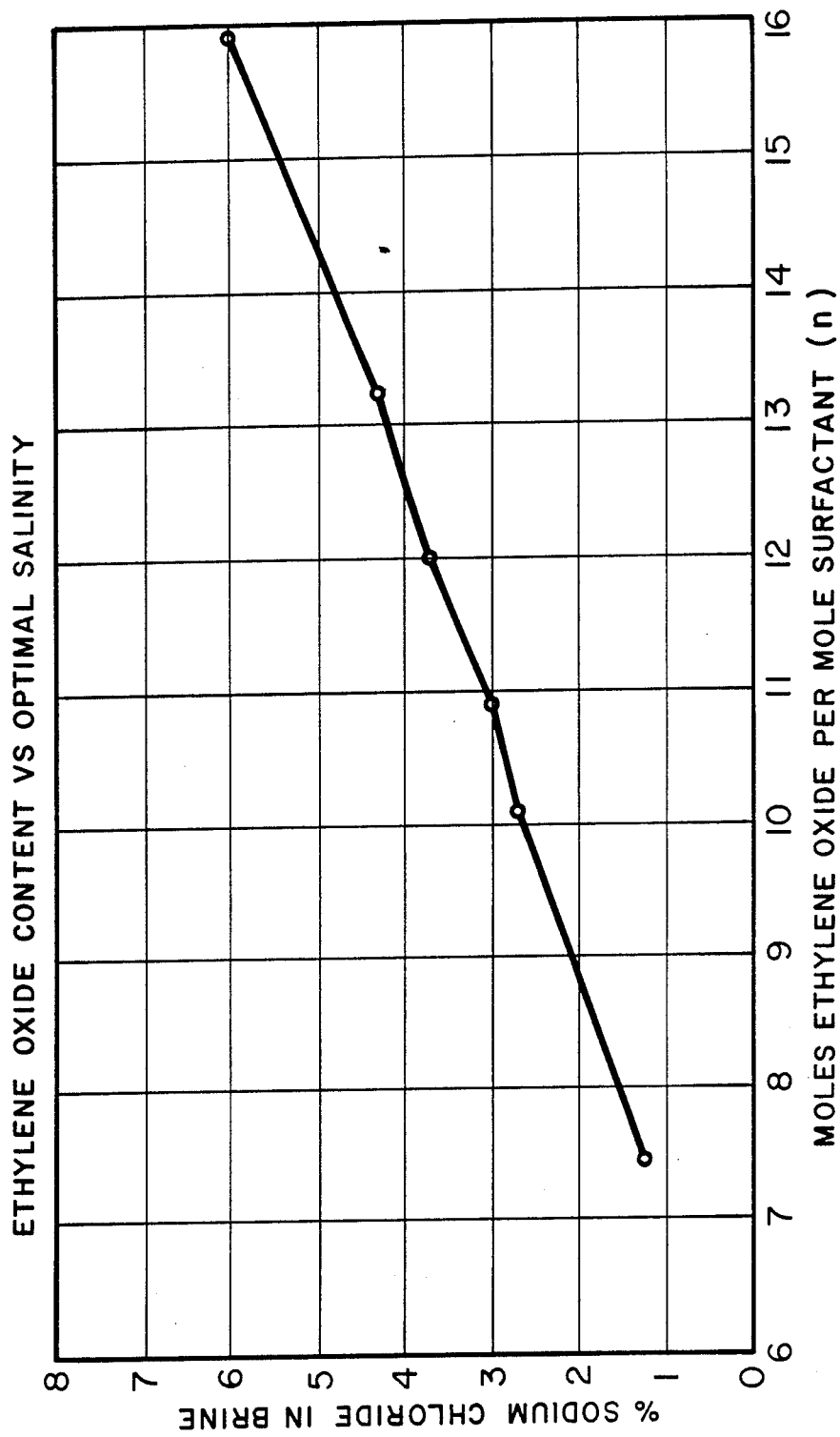

WATER-FLOOD SURFACTANT

The present invention relates to non-ionic detergents capable of use as water-flood additives. More particularly, this invention relates to new nonionic detergents and their method of manufacture by ethoxylation of an oil-soluble natural petroleum sulfonate.

BACKGROUND OF THE INVENTION

Water flooding and surfactant flooding are processes well known in the art to recover the vast quantities of oil which remain in the formation after primary oil recovery operations. Designing new surfactants and surfactant systems of high oil recovery efficiency is a critical step toward advancing this technology.

To be effective in liberating oil from a petroleum reservoir, a surfactant must, in general, be able to reduce the interfacial tension between oil and aqueous reservoir fluid from around 30 dynes per centimeter to a few millidynes per centimeter or less. The mahogany sulfates referred to in this disclosure are able to accomplish this; however, their performance is limited to use in fresh or very slightly saline water. Since very few reservoirs normally contain fresh water as their aqueous phase, the use of mahogany sulfonates has been limited to experimental plots in which an attempt to replace the brine with fresh water was tried. The replacement process, with the accompanying need to dispose of the old brine, has proved ineffective. Also, the replacement of aqueous reservoir fluid with a fluid of less salinity has introduced deleterious changes to the reservoir, not all of which are completely understood.

Ordinary commercial non-ionic detergents are able to function in brine, but the minimum interfacial tension achieved by these is generally too high to be useful, being usually well over one dyne per centimeter.

The purpose of this invention has been to synthesize a surfactant which will give a low interfacial tension (5 millidynes per centimeter, or less) between reservoir oil and reservoir brine. In addition, it was intended that, by proper adjustment of surfactant composition, a specific member of a given category of surfactant could be made to suit the salinity of any reservoir.

Work on this surfactant has proceeded from certain definite theoretical premises:

(1) The surfactant will contain a hydrophobic part and a hydrophilic part. These will be opposite ends of a long molecule. The molecule will tend to orient at an interface with its hydrophobe in the oil and its hydrophilic portion in the aqueous phase.

(2) The hydrophobic part should have, as nearly as possible, the same solvency as the reservoir oil. This means that the hydrophobe should have no tendency to clump together, rather, they should comingle freely with the oil molecules. An extremely unfavorable case would be that of a fluorocarbon hydrophobe. The fluorocarbon is not soluble in oil, and a surfactant made therefrom is ineffective. Even such differences as those between normal paraffin chains and "iso" (branched) chains prevent perfect solvency. The difference in solvency of normal and iso paraffin chains is quantified in "The Solubility of Nonelectrolytes", by Hildebrand and Scott, Third Edition, Dover Publications, Inc., New York. In the Appendix I "Selected Values of Solubility Parameters", the parameter $\delta$ for n-octane is 7.55, while the $\delta$ for 2,2,4 trimethyl pentane is 6.85.

The hydrophilic part of the surfactant should be compatible with brine, even a hard brine, containing ions of calcium and magnesium. The poly(ethylene oxide) chain has this compatibility. The poly(ethylene oxide) chain has the configuration: —CH$_2$—CH$_2$—O—CH$_2$—CH$_2$—O—CH$_2$—CH$_2$O—H.

It can be produced with any degree of polymerization. The formula above contains three ethylene oxide units. The poly(ethylene oxide) chain owes its solubility in water to the fact that the oxygen atoms can hydrogen-bond to some of the water molecules. This bonding persists when the aqueous phase becomes a brine; however, two hindrances are brought into play. First, many water molecules are tied up in bonding to the ions of the salt (or salts). The water, in effect, becomes less concentrated, and the poly(ethylene oxide) chain must extend farther (be longer) in order to maintain the same bonding force it had in pure water. Secondly, many of the oxygen atoms of the chains are bonded with cations of the salt (or salts). Fortuitously, the latter effect is mitigated by the fact that the cations themselves are hydrated (bonded to water). Thus, the poly(ethylene oxide) chain retains a solvency which is compatible with brine. It is obvious, however, that, the more concentrated the brine, the longer must be the poly(ethylene oxide) chain used to generate a hydrophilic force which can compete with attractions at the hydrophobe, so as to hold the surfactant molecule at the interface. These conditions lead to the next statement.

(4) The surfactant should have the correct hydrophile/lyophile balance (HLB). In other words, the hydrophilic portion should be large (long) enough to keep the hydrophobe from pulling the whole molecule into the oil. Likewise, the hydrophobe should be large enough to prevent the hydrophilic chain from pulling the molecule into the aqueous phase. The proper HLB leaves the molecule balanced at the interface.

In connection with HLB, it should be noted that an increase in temperature, which causes a faster break-up of hydrogen bond, has a similar effect to that of an increased brine concentration in making the ethylene oxide chain less hydrophilic. Hence, at higher temperatures, a longer ethylene oxide chain must be used to generate the same hydrophilic force.

(5) Since the surfactant molecule must stay in the interface in order to lower the interfacial tension it must be heavy enough that normal thermal perturbation do not displace it into one phase or the other. Short chain acids (caproic, capryllic, and capric, e.g.) are known to not even make useful soaps. From a typical soap-former, stearic acid ($C_{18}H_{35}COOH$) we get the $C_{18}H_{37}$-radical. However, this radical with suitable ethylene oxide addition to yield $C_{18}H_{37}$—$[OCH_2CH_2]_n OH$ does not have enough molecular weight to keep it in the interface so as to obtain millidyne/centimeter interfacial tensions. The octadecyl($C_{18}H_{37}$-) radical has a molecular weight of 253, while the molecular weight considered effective in this application is in the range 300 to 500.

(6) It can be noted that the first criteria for a water-flood surfactant are structural and thermodynamic in nature. From the method of use of such surfactants, there is also a requirement which is kinetic in nature; i.e., the surfactant must be able to move into and out of the surface in an unhindered manner. The surfactant, in use, is dissolved in the brine phase. As it contacts oil, fingering of oil occurs, along with emulsion and coacervate formation. These processes multiply greatly the interfacial surface and require that appropriate amounts of surfactant move into the surface. Whenever a massive bank of oil can be formed as it moves through the formation, interfacial surface must decrease, and surfactant must move out of the interfac. Alternatively, if produced at the well-head as an emulsion, it is desirable that the oil separate to the top in a resonable time, say 24 hours. Thus, the surfactant is not an emulsifier in the usual sense, producing, as it does, an unstable emulsion.

Research leading to the subject of this invention was directed toward the synthesis of a surfactant which would meet the six criteria heretofore outlined.

No particular attention was paid to meeting criterion (1), since the criterion mentioned there is a typical one for surfactants. In order to meet criterion (3), that of hydrophile solvency, it was necessary to go to the poly-(ethylene oxide) chain, since it is the only feasible hydrophile group known which is compatible with strong brine. The use of the poly(ethylene oxide) chain makes it easy to meet criterion (4), since the chain can be synthesized to any needed number of units (n).

No means of achieving criterion (6) was known; its attainment was pure serendipity.

To attain the hydrophobe of perfect solvency, as per criterion (2), it was considered that there would be no better way to secure a hydrophobe compatible with an oil than to take the hydrophobe from the oil itself. At the same time, the molecular weight criterion (5) could be achieved through the utilization of a fraction of the oil of sufficiently high molecular weight.

In the actual synthesis of the detergent, there is a detail which has not been heretofore addressed, namely: the provision of a reactive group to the hydrophobe to which an ethylene oxide chain could be attached. In general, the reactive groups suited to this purpose are:
—OH—(either alcohol or phenol)
=NH—secondary amine
—NH$_2$—primary amine
—CONH$_2$—amide
—COOH—carboxyl
—SH—thiol
—COH—aldehyde glycerol or glyceride or saccharide The common feature of these groups is that of a hydrogen atom which can be ionized very sparingly. Groups which ionize strongly, as the sulfate (—SO$_4$H) and sulfonate (—SO$_3$H) groups are not suitable.

An ideal source for hydrophobic material is found in the alkaline mahogany sulfonates, such as those produced by the Sonneborn division of Witco Chemical Company. These are produced as a by-product in the refining of white mineral oil. In the process, a higher-boiling fraction of a paraffin base crude is treated with fuming sulfuric acid or oleum. Portions of the crude, especially those molecules containing aromatic and heterocyclic rings are sulfonated and are dissolved in the acid phase. The acid phase, containing sulfonic acids, is separated from the reaction mixture and is washed with water. The water treatment separates the sulfonic acids into "green acids, which are soluble in the water and "mahogany acids" which are oil-soluble and remain in an oil layer. Neutralization of the oil layer gives the "mahogany sulfonates" of commerce.

The mahogany sulfonates of Witco are sold under the trade name "Petronate." Four of the most useful Petronates span an "equivalent weight" range of from 410 to 510. Considering that the —SO$_3$Na group has a molecular weight of 103, the hydrophobe molecular weight of the series runs from 307 to 407. For the first application of this invention, the medium weight Petronate HL (Equivalent Weight=440–470) was tried. Since a sulfonate cannot be treated with ethylene oxide, the first consideration concerned the feasibility of treating the Petronate with sodium hydroxide so as to produce a phenol (or possibly an alcohol).

$$RSO_3Na + NaOH \rightarrow ROH + Na_2SO_3$$

It was possible to do this at atmospheric pressure in the equipment available. The reaction was even carried to the melting point of sodium hydroxide (318°) without loss of Petronate by boiling. This was an unexpected result which was of great convenience.

The second consideration involved the feasibility of reacting the phenol mixture with ethylene oxide without a difficult purification step to remove the by-product sodium sulfite. As attested by results presented here, it was possible to proceed without the purification step. (This was unexpected, but of great importance.)

THE INVENTION

The present invention involves the successful conversion of Petronate HL to a non-ionic surfactant having a calculated amount of from 7.4 to 16 moles of ethylene oxide added per mole of hydrophobe. (Petronate is a registered trademark of Witco Chemical Corporation.)

The drawing is a graph of ethylene oxide content versus optimal salinity.

The starting material, Petronate HL, is manufactured and sold by the Sonneborn division of the Witco Chemical Corporation. The Petronate HL as described in the Witco and Sonneborn literature refers to a "Sonneborn sulfonate made from natural petroleum crude." The specifications of the Petronate HL are as follows:

| Specifications | Petronate HL |
|---|---|
| Sulfonate (%) | 61–63[a] |
| Water (%) | 4–5 |
| Equivalent Weight | 440–470 |
| Color[b] | 4–5B |

| Typical Tests | Petronate HL |
|---|---|
| Mineral Oil (%) | 32.5 |
| SO$_3$ content (%)[c] | 17.5 |
| Ash (%)[d] | 15.5 |
| Furol viscosity (sec)[e] | 135 |
| Flash point (°C.) | 193 |
| (°F.) | 380 |
| Fire point (°C.) | 213 |
| (°F.) | 415 |
| Density (lb/US gal) | 8.5 |

[a]Di-Petronate sulfonates contain 52.0% active sulfonates
[b]Lovibond, 10% in white oil, ½" cell.
[c]Dry, oil-free basis.
[d]As Na$_2$SO$_4$
[e]At 100° C. (212° F.)

455 gms Petronate HL (approximately 1 mole) were weighed into a stainless steel reactor pot. 86 grams of NaOH were added on top of the Petronate, and the vessel was closed for heating and stirring. The amount of the sodium hydroxide was 6 grams in excess of the amount required to convert the sulfonate to phenol and the phenol to sodium phenolate.

The reactor was heated and stirred until it reached 319° C., the melting point of NaOH. It was maintained at a temperature over 318° C. for an hour; then, it was cooled to the vicinity of 200° C. At all times while heating, a gentle current of nitrogen gas was passed through the top of the reactor to protect the contents from fire and from slow oxidation, and to remove volatiles. No properly designed condenser was available; however, an "air condenser" comprising a length of Tygo tubing permitted the collection of some water (about 17 grams) and a quantity of light yellow oil (final quantity=53.0 grams).

A stainless steel sparger was inserted beneath the melt to facilitate the addition of ethylene oxide gas. In order to facilitate the reaction of ethylene oxide with the phenolate, 5 grams of ethylene oxide were rapidly purged through the vessel to clear out nitrogen and establish an atmosphere of ethylene oxide. The vessel was then attached to a water manometer to indicate the demand for more reactant as it was used up. Thereafter, anytime the rate of reaction fell off, a 5 gram purge of ethylene oxide was made in order to remove volatile interferences and re-establish a favorable concentration of ethylene oxide. Later in the run, 10 gram purges were found to be more effective. No part of the ethylene oxide purge was counted in the running total of ethylene oxide reacted. The logic of this is borne out by the final approximate mass balance.

The initial part of the run was spent in searching from 160° to 200° C. for a suitable reaction temperature. In spite of frequent purgings, the rate of addition of ethylene oxide always settled back to 8 grams (0.18 mole) per hour. When 65 grams (1.48 moles) had been added, a short nitrogen purge was made at 200° C. No improvement in rate resulted, so that temperature was raised to look for a better rate. At 225° C., so much gas starting coming off that it had to be vented. Blowing with nitrogen at 200° C. for 45 minutes did not help much. Next day, the liquid was blown with nitrogen for 3 hours at temperatures from 200° to 272° C. Considerable light yellow, pungent oil was recovered.

Ethoxylation was resumed at 193° to 213° C. with the rate still at 8 grams per hour up to 2.80 moles added. After 193 grams (4.4 moles) had been added, the reaction around 210° C. increased to a rate of from 16 to 40 grams per hour (0.36 to 0.91 moles/hour).

Rates for the rest of the addition were satisfactory. The targeted control point was between 210° and 220° C.

The recovered non-ionic was a light gray-tan deliquescent solid, whereas the petronate had been a dark brown (mahogany) extremely viscous liquid. The melting point was not determined; however, the product was still liquid when cooled to 100° C. The run number identification of the product was CAS I-13.

The reactions involved are:

R—SO$_3$Na+NaOH→ROH+Na$_2$SO$_3$

ROH+NaOH→RONa+H$_2$O

RONa+nCH$_2$CH$_2$O→R—O[—CH$_2$—CH$_2$—O]-$_n$—Na.

The product is largely hydrolyzed to R—O[CH$_2$CH$_2$O]$_n$H, and, in all cases, n is an average ethoxylation distribution The initial mass balance is as follows:

| | |
|---|---|
| Petronate HL | 455 grams |
| NaOH | 86 |
| Volatile oil | −53 |
| H$_2$O from Petronate HL | −20 |
| H$_2$O from reaction | −18 |
| | 450 grams |
| Product containing ethylene oxide | 1,094 grams |
| Remaining content of other material | −450 |
| Ethylene oxide in product. | 644 grams |
| Ethylene oxide supposedly added (weighed in) | 736 grams |
| | −644 |
| Ethylene oxide shortage in product | 92 grams |

The 92 gram "lack of closure" is a discrepancy of 8.4%. Not all of the product was weighed, since some stuck to the stirrer, sparge, and thermowell. Also, not all the volatile oil was recovered, due to the lack of a condenser; and, the ethylene oxide weighed in and apparently reacted may not have all "stuck". So, we can divide the 92 gram discrepancy three ways, adding to the product weight and volatile oil and subtracting from the ethylene oxide weighed in.

[92/3=31, approximately]

The adjusted mass balance is:

| | |
|---|---|
| Petronate HL | 455 grams |
| NaOH | 86 |
| Volatile oil | −53 less 31 |
| H$_2$O from Petronate HL | −20 |
| H$_2$O from reaction | −18 |
| Product - ethylene oxide | 419 grams |
| Product: 1,094 grams + 31 grams = | 1.125 grams |
| | −419 |
| Ethylene oxide added, by difference | 706 grams |
| Ethylene oxide weighed in | 736 grams |
| less correction | −31 |
| Ethylene oxide added | 705 |
| Moles ethylene oxide: | 705/44 = 16.0 |

Product no. CAS I-13 was the "discovery" product for the type of surfactant claimed in this application. In its preparation, the mark for saline compatibility was considerably over-shot in that the material functioned optimally in a 6% NaCl brine. One percent of CAS I-13 in 6% NaCl brine gave an interfacial tension measurement against n-octane of 3 millidynes/centimeter.

In order to get a product which would function in field brines of around 3 percent NaCl, another series of products was made with product numbers:

CAS II-16
CAS II-18
CAS II-19
CAS II-21
CAS II-23

The procedure was the same as before, except that 50 grams of NaOH were used instead of 86. This was done both to conserve ingredients and to minimize corrosion of the 316 stainless steel pot. The fact that the reaction proceeded in essentially the same manner demonstrate that not all the phenol need be converted to phenolate in order to have good catalysis. The first three samples in the above list were small "pilot" samples of approximately 10 grams each. Sample CAS II-21 was approximately 100 grams, while CAS II-23 was the rest of the pot. In this manner, one run was able to give 5 separate product samples. Also, it demonstrated the manner in which a batch of surfactant in a plant could be brought "on specification" with appropriate pilot testing.

The five products were put through a standard salt scan by NIPER in order to determine the salt concentrations at which each would function. Salt scan values are listed below:

| Sample | Ethylene oxide, approx. $\underline{n}$ | Brine % NaCl |
|---|---|---|
| CAS II-16 | 7.45 | 1.25 |
| CAS II-18 | 10.1 | 2.7 |
| CAS II-19 | 10.9 | 3.0 |
| CAS II-21 | 12.0 | 3.7 |
| CAS II-23 | 13.2 | 4.3 |
| CAS I-13 | 15.9 | 6.0 |

The data are plotted in the drawing. Although the values are somewhat approximate (due to difficulties with a mass balance), the thesis is adequately supported that any salinity (at least up to 6% NaCl) can be matched with a surfactant of appropriate length of ethylene oxide chain.

It is believed that no difficulties were encountered which could not be more easily solved in a full sized plant. In particular, the ability of a commercial plant to use pressure in the ethoxylation step would be quite beneficial. The increase in rate of addition of a gaseous reactant with increased partial pressure of that reactant is a well-established principle of chemical kinetics. Admittedly, some of the rates encountered in this study need to be increased. Also, in this study, a problem was encountered when the release of volatile oils interferred with the estimate of ethylene oxide demand by means of a water manometer. In a pressurized vessel, a presure could be held which would keep the volatile oil liquid, while a measurable drop in the superimposed ethylene oxide pressure could signal a demand for more ethylene oxide. At the same time, the build-up of ethoxylated product in the pot could be monitored by any one of a number of liquid content gauging methods. The product can be made from any one of a number of natural petroleum crudes. Possible uses of the product are as follows:

waterflood detergent (especially for brine)
well clean-out agent
drilling mud emulsifier for both oil and water-based mud.
detergent for asphalt emulsions
ocean water detergent (especially for naval and maritime use)
detergent for dirty laundry (oily)

Other uses which can be anticipated from the above indications can be surmised.

In general, a specific brine will require a detergent of a specific number of added moles of ethylene oxide to function optimally; stronger brines requiring more moles of ethylene oxide. Conversely, a given detergent composition will have a certain brine concentration which is optimum for it.

PHASE BEHAVIOR SCANS

Phase partitioning tests, salinity scans and EACN scans, of the ethoxylated petroleum sulfonate formulations with and without added alcohol were conducted at 50 C. using sealed 10 ml disposable glass pipets. Equal volumes of brine containing the surfactant formulation and oil were placed in the pipet. The tubes were sealed and then warmed to 50 C. in a constant temperature bath. The tubes were vigorously shaken and allowed to stand overnight. Phase volumes are read and the tubes returned to the bath and reread the following week. Once constant readings are obtained (this requires from hours to weeks depending upon the viscosity of the solutions and the proximity to optimal salinity), the solubilization parameter is calculated for the three phase system.

ILLUSTRATIVE COREFLOOD

The following procedure was used in preparing the water-wet Berea sandstone cores used for surfactant flooding. Berea cores, 10 inches long and 1.5 inches in diameter were weighed to determine the dry weight before saturation with brine of the desired salinity. The cores were placed in an evacuation chamber and a vacuum of about 1 mm was pulled on the core for 2 hours. The core was saturated under partial vacuum with degassed brine and allowed to remain under vacuum for one hour. The core was removed from the evacuation chamber and weighed to determine saturated core weight. The pore volume of the core was calculated by the relationship: brine saturated core weight (g)—dry core weight (g) divided by the density of the brine (g/ml) equal to the core pore volume (ml). The core was then mounted wet in a Hassler sleeve and brine (2 pore volume) was pumped through the core before determining the original permeability to brine. The Hassler is thermostatically heated to simulate reservoir temperature.

The brine-saturated core was oil flooded at 30 ft/day to remove all the displaceable water. The oilflood was carried out using a recycling oil system and required 24 hours. The total water displaced by the oil saturation was used to calculate oil saturation, Soi, (original oil saturation). Optionally, oil permeability was determined in a manner analogous to that used above for establishing original permeability to water. Prior to waterflood, the core effluent line was air blown to remove oil.

The oil flooded core was waterflooded at 3 to 5 feet per day, until the effluent water: oil ratio is greater than 99:1. The total oil displaced is measured and Sow, (oil saturation at the end of the waterflood) is calculated. The residual oil volume remaining in the core is calculated by subtracting the oil volume displaced by the waterflood from the water volume displaced by the oilflood. If desired, water permeability after waterflood can be determined in a manner analogous to that used above for original permeability to water. Cores were routinely conditioned in this manner prior to carrying out surfactant flooding tests. At this point, the core simulated an oil reservoir that had been exhaustively waterflooded. The surfactant slug containing the ethoxylate is injected at a slower rate, corresponding to field flow rates of one foot per day as stated for the pore volume specified. The slug may optionally contain a mobility buffer or be followed by a mobility buffer. Oil recovery from the core is measured to determine Soc, final oil saturation after chemical flooding. Oil recovery efficiency of the chemical flooding, R, is calculated as (Sow-Sow/Soc)×100.

The following are examples of displacement experiments which demonstrate the feasibility of the present method.

EXAMPLE 1

A coreflood (OFCR 1) at the reservoir temperature of 50 C., using North Burbank Crude as the oil and a brine, formulated from 50:50 North Burbank Brine and Ark Burbank fresh water, was prepared as above and water flooded to residual oil saturation. A displacement experiment conducted at one foot per day used a surfactant formulation (1.17 pore volume slug) of 3% CAS II-23 which has an average EO content that has 1000 ppm Flocon* 4800M biopolymer added as viscosifier. The IFT of the formulation against NBU crude oil is 26 millidyne/cm at 50 C. A mobility buffer (1.1 pore volume) of 2000 ppm Flocon 4800M biopolymer was injected to displace the surfactant. The North Burbank brine contain about 6.65% NaCl, 1.53% $CaCl_2$. Ark Burbank water is nearly fresh and contains only 600 ppm NaCl. A summary of the coreflood is presented below:

| Core  | Soi   | Sow   | Soc   | Re    |
|-------|-------|-------|-------|-------|
| OFCR1 | 69.49 | 42.81 | 14.46 | 66.23 |

The above is a registered trademark of Pfizer Inc.

The surfactant formulation recovered 66% of the oil remaining after waterflood. No attempt was made to optimize slug size wherein the above is far in excess of what is required for oil recovery.

What is claimed is:

1. A method of making a non-ionic surfactant having a hydrophobic part and a hydrophilic part which comprises the steps of mixing, in a reactor, sodium hydroxide with a sulfonated product of a natural petroleum crude, the sodium hydroxide being in excess of the amount required to convert the sulfonate to phenol; heating the mixture while stirring to about 140° to 319° C. for a period of at least one hour; passing a current of inert gas through the top of the reactor during the heating step; cooling the mixture to a temperature of approximately 200° C. while continuing to pass an inert gas through the top of the reactor; and passing ethylene oxide gas through the mixture in the reactor while maintaining the temperature in the reactor between 120° and 220° C. and allowing the use of pressure to increase the rate of reaction.

2. A method of making a non-ionic surfactant as set forth in claim 1, wherein the mixture is heated, while stirring, to a temperature of about 319° C. for about one hour.

3. A method of making a non-ionic surfactant as set forth in claim 1 wherein the ethoxylation temperature is in the range of 200° to 220° C.

4. The method of claim 1 in which the sulfonated product of a natural petroleum crude is a mahogany sulfonate.

5. The composition of matter achieved in claim 1, in which the product is a non-ionic surfactant with the hydrophobic part derived from a high molecular weight portion of a natural petroleum crude and the hydrophilic part is a poly(ethylene oxide) chain of appropriate length to function as a surfactant in an oil reservoir brine of particular salinity.

6. The product of claim 5 in which the molecular weight of the molecules from natural crude used to form the hydrophobic part of the surfactant fall in the range of 260 to 600.

7. The product of claim 6 in which the molecular weight of the molecules from natural crude used to form the hydrophobic part of the surfactant fall in the range of 300 to 410.

8. The product of claim 5 in which the hydrophobic portion of the surfactant is derived from the identical crude to be produced.

9. The product of claim 5 in which the hydrophobic portion of the surfactant is derived from a crude similar in composition to the one to be produced in the field.

10. The product of claim 1 in which the sulfonated product of a natural petroleum crude is a mahogany sulfate.

11. A method for emulsifying water and oil and oily-based materials which comprises adding to the water and oil and oily materials a non-ionic surfactant product comprising: a sulfonated natural petroleum crude which has been treated with excess sodium hydroxide at about 140 C. to 319 C. to convert the sulfonate to a phenol and subsequently to a sodium phenolate followed by treatment with ethylene oxide at about 120 to 220 C.

12. A method according to claim 11 wherein said surfactant product is added during waterflood oil recovery operations.

13. A method according to claim 11 wherein said surfactant product is added as an oil well clean-out agent.

14. A method according to claim 11 wherein said surfactant product is added as a drilling mud emulsifier with oil and water based muds.

15. A method according to claim 11 wherein said surfactant product is added as a detergent for asphalt emulsions.

16. A method according to claim 11 wherein said surfactant product is added as an ocean water detergent for naval and maritime use.

17. A method according to claim 11 wherein said surfactant product is added as detergent for dirty and oily laundry.

18. A nonionic surfactant having a hydrophobic portion and a hydrophilic portion and capable of producting extremely low (millidyne/cm range) interfacial tensions between petroleum oils and a brine, the composition of said surfactant being such that is hydrophobic portion is a high molecular weight hydrocarbon radical having perfectly compatible solvency with said petroleum oil and its hydrophilic portion being a polyethylene oxide chain of such length as to be most optimally solvated by the brine at given conditions of salinity and temperature.

19. The product of claim 18 in which the functional group enabling the hydrophobe to be reacted with ethylene oxide is one from a set of functional groups consisting of: primary amine, secondary amine, amide, carbonyl, thiol, aldehyde, glycol, glycerine, or saccharide, where the functional group can be present in the original petroleum fraction or be added through chemical reaction.

* * * * *